United States Patent [19]
Ferrante et al.

[11] Patent Number: 5,689,757
[45] Date of Patent: Nov. 18, 1997

[54] METHOD AND APPARATUS FOR DETECTING SUBSTRATE ROUGHNESS AND CONTROLLING PRINT QUALITY

[75] Inventors: John L. Ferrante, Williamson; Leela Ganguly, Webster; J. Stephen Kittelberger, Rochester; Kathryn A. Wallace, Canandaigua; Joseph R. Weber, Rochester, all of N.Y.

[73] Assignee: Xerox Corporation, Stamford, Conn.

[21] Appl. No.: 509,017

[22] Filed: Jul. 28, 1995

Related U.S. Application Data

[63] Continuation of Ser. No. 276,573, Jul. 18, 1994, abandoned.
[51] Int. Cl.⁶ .................................................... G03G 21/00
[52] U.S. Cl. .......................... 399/45; 356/371; 356/446
[58] Field of Search ............................ 356/371, 446; 355/208, 311; 399/45

[56] References Cited

U.S. PATENT DOCUMENTS

| | | | |
|---|---|---|---|
| 4,338,017 | 7/1982 | Nishikawa | 355/272 |
| 4,364,663 | 12/1982 | Gardner et al. | 356/371 |
| 4,553,033 | 11/1985 | Hubble, III et al. | 250/353 |
| 4,897,670 | 1/1990 | Hasegawa et al. | 347/193 |
| 4,950,905 | 8/1990 | Butler et al. | 250/358.1 |
| 4,989,985 | 2/1991 | Hubble, III et al. | 356/445 |
| 5,053,822 | 10/1991 | Butler | 355/246 |
| 5,287,154 | 2/1994 | Nakai et al. | 355/208 |

FOREIGN PATENT DOCUMENTS

| | | | |
|---|---|---|---|
| 61-83069 | 4/1986 | Japan. | |
| 62-2111 | 1/1987 | Japan | 356/371 |
| 62-2114 | 1/1987 | Japan | 356/371 |
| 63-297074 | 12/1988 | Japan. | |
| 4-358189 | 12/1992 | Japan. | |
| 1024708 | 6/1983 | U.S.S.R. | 356/371 |
| 1249324 | 8/1986 | U.S.S.R. | 356/371 |
| 1539529 | 1/1990 | U.S.S.R. | 356/371 |

*Primary Examiner*—F. L. Evans

[57] ABSTRACT

A method and apparatus for determining the level of roughness in a paper or other substrate to be processed in a machine, and for correspondingly adjusting the machine parameters that are affected by the different levels of substrate roughness, before the substrate is processed through the machine.

2 Claims, 3 Drawing Sheets

METHOD AND APPARATUS FOR DETECTING SUBSTRATE ROUGHNESS AND CONTROLLING PRINT QUALITY

This is a continuation of application Ser. No. 08/276,573, filed Jul. 18, 1994 now abandoned.

FIELD OF THE INVENTION

This invention relates to optimizing copy quality and machine operating parameters in substrate marking technologies by determining the level of roughness of a substrate, and correspondingly adjusting substrate processing operations therewith.

BACKGROUND OF THE INVENTION

Copy quality is sensitive to the level of roughness of the copy sheet in marking technologies such as electrostatographic reproduction of images, e.g. electrophotography, and laser printing, as well as thermal ink jet, and thermal transfer reproduction of images. Distinct variations exist as to the level of paper roughness found in individual copy sheets, such as paper, (hereinafter referred to as "substrates") that are used in a substrate marking machine. Various machine parameters are affected by the level of roughness found on a particular substrate to be processed through the machine. Based on the substrate roughness level, these parameters can be adjusted for their optimum functionality within the machine as well as for achieving optimum copy quality. For example, an ideal goal in electrophotography is to have the correct amount of toner deposited onto a copy sheet on a continuous basis. With poor development control two situations occur. First, concerning a variability of toner quantity applied, too little toner creates lighter images, where too much toner creates darker images and may cause toner to appear in non-image areas. Second, concerning the machine, too much toner development causes excess toner waste which both increases the expense of running the machine and wears machine components at a faster pace. Replacement or repair of these components is thereby required on a more frequent basis. The need for precise toner control is intensified in color development systems where individual color images are superimposed on each other to create the full color image.

A rougher substrate contains a greater surface area than a smoother substrate, and may therefore require application of a higher developed toner mass per unit area to get the same dark, uniform, sharp copy quality. Additionally, if a greater amount of toner is required on a rougher substrate, the development voltage, and/or the toner concentration, and/or the fuser set temperature must be raised to assure that the toner is completely fused to the paper. Under-fused toner on a substrate creates the possibility of smears, streaks or blurred copies. An increased voltage may also be required for the corona generating devices associated with both the charging element, as well as the transfer element, for a rougher surface substrate requiring a greater amount of toner deposited thereon. Uniformly increasing machine parameters such as the fuser set temperature, fuser dwell time, or voltage level to the charging device, transfer device or developer may eliminate certain copy quality problems on rougher surface papers, however, other negative factors are thereby created. For example, increased wear on these affected components causes the need for more frequent component repair or replacement. Furthermore, the increased power required to run the component at the higher settings results in increased energy consumption and cost. Machines that can optimize copy quality as well as internal processing operations will have a greater latitude of operation and a competitive edge.

It is known in the electrical graphic arts to use light sensors for measuring the density of a powderous or liquid substance. One such sensor is a developability sensor, also known as a densitometer, used to monitor the "Developed Toner Mass Per Unit of Area," referred to as DMA. A densitometer acts, generally, when toner is illuminated with a collimated beam of light from an infrared light emitting diode (LED), to measure the level of specularly reflected light therefrom. Light is either specularly reflected, scattered or absorbed. In the case of DMA measurement, toner development onto a substrate correspondingly increasingly attenuates the intensity of the light specularly reflected. The attenuation is the result of either absorption of the incident light in the case of black toners, or by scattering of the incident light away from the specular reflection angle, as in the case of colored toners. Thus, at a high DMA quantity, there is only a very small specular signal, and at a low DMA quantity, there is a higher specular light signal. A densitometer is described, for example, in U.S. Pat. Nos. 5,053,822, 4,553,033, 4,950,905, and 4,989,985. Limitations exist, however, with this type of sensor in terms of achieving optimum copy quality and machine performance. For example, the densitometer requires one or more sheets to have run through the system before the DMA quantity can be detected and then adjusted, as the sensors associated with a densitometer can only measure the DMA while the sheets are being processed through the machine during or after the toner application process. Thus, toner density cannot be monitored on an individual sheet basis, and varying levels of substrate roughness cannot be accommodated from one sheet to the next. Furthermore, dynamic-based sensing systems, such as a densitometer, are more prone to inaccuracies in measurements and the more frequent need for adjustments and calibration to the sensing components. Furthermore, this type of developer quantity control does not accommodate for automatic adjustments in those machine parameters that can be correspondingly controlled for optimum copy quality with respect to the level of roughness of an individual copy sheet or substrate, before that particular substrate is processed through the machine.

In response to these problems, a need exists for a static manner for determining the level of roughness in a substrate to be processed in a machine, and for correspondingly adjusting the machine parameters that are affected by the different levels of substrate roughness, particularly, before the substrate is processed through the machine.

As a result, the present invention provides a solution to the described problems and other problems, and also offers other advantages over the prior art.

SUMMARY OF THE INVENTION

In accordance with the invention and in accordance with one aspect of the invention, there is provided an apparatus for detecting a roughness level of a substrate. The apparatus comprises a light source for projecting light rays on the substrate. A light sensing device, in a light receiving relationship with light reflected from the substrate, detects a level of specularly reflected light from the substrate and generates a first signal in response thereto. The level of diffusely reflected light is also detected and a second signal generated in response thereto.

In accordance with another embodiment of the invention, there is provided a substrate marking machine capable of detecting the level of roughness of a substrate. The machine comprises a light source for projecting light rays on the substrate. A light sensing device, in a light receiving relationship with light reflected from the substrate, detects a level of specularly reflected light from the substrate and generates a first signal in response thereto. The level of diffusely reflected light is also detected and a second signal generated in response thereto.

In accordance with another embodiment of the invention, there is provided a method for detecting the level of roughness of a substrate. The method for detecting the level of roughness of a substrate comprises the steps of projecting lights rays on the substrate, detecting a level of specularly reflected light from the substrate and generating a first signal in response to said detected level of specularly reflected light, and detecting a level of diffusely reflected light from the substrate and generating a second signal in response to said detected level of diffusely reflected light. The method of the present invention also comprises the step of determining a ratio value as a function of the first signal and the second signal.

DETAILED DESCRIPTION OF THE DRAWINGS

The paper roughness determination system of the present invention can be utilized in a variety of types of equipment which perform marking operations on conventional paper or other sheets ("substrates") which vary in degrees of level of paper roughness. For example, it is understood by one skilled in the art that thermal transfer marking used in facsimile transmission of images, thermal ink jet, electrostatographic reproduction, and laser printing are a few of the applications that find utility in the present invention. For purposes of illustration, the invention is described in the context of electrophotographic printing or reproduction equipment for forming images on a substrate.

Figure 1:
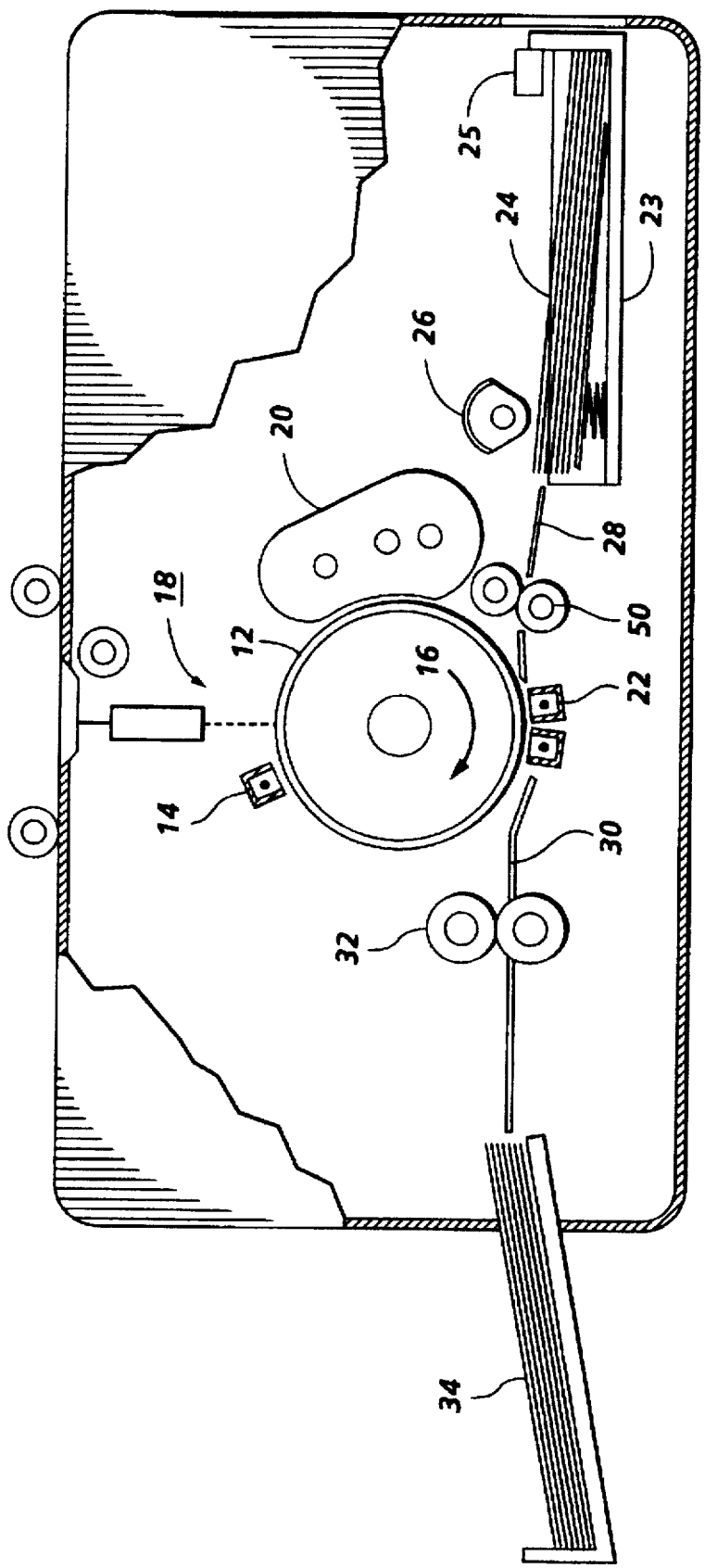
FIG. 1 is an elevational view of a reproduction machine in which the present invention can be utilized.

With reference to FIG. 1, there is illustrated an electrophotographic printing machine having a photoconductive surface 12 movable in the direction of arrow 16 to advance the photoconductive surface sequentially through various processing stations. In a preferred embodiment, substrate roughness detection apparatus 25 is located in supply tray 23 so that the roughness of the substrate can be accurately measured while the substrate is in a static state, and also so that the output signal from the detector 25 can be processed through a microprocessor and adjustments made to machine parameters before the substrate is processed through the machine. It is understood, however, that the substrate roughness detector of the present invention can be positioned at other locations in a machine. Surface roughness detection apparatus 25 will be described in detail with reference to FIGS. 2 through 5.

At a charging station, a corona generating device 14 electrically connected to a high voltage power supply charges the photoconductive surface 12 to a relatively high, substantially uniform potential. Next, the charged portion of the photoconductive surface 12 is advanced through exposure station 18. At exposure station 18, an original document is positioned on a transparent platen. Lamps illuminate the original document and light rays reflected from the original document are transmitted onto photoconductive surface 12. A magnetic brush development system 20 advances a developer material into contact with the electrostatic latent image on surface 12.

At transfer station 22, a sheet of paper is moved into contact with the toner powder image. The paper sheet 24 is advanced to the transfer station by sheet feeding apparatus 26 contacting the uppermost sheet of the stack. Sheet feeding apparatus 26 rotates so as to advance sheets from the stack onto transport 28. The transport 28 directs the advancing sheet of paper into contact with the photoconductive surface 12 in timed sequence in order that the toner powder image developed thereon contacts the advancing sheet of paper at the transfer station. Transfer station 22 includes a corona generating device for spraying ions onto the underside of the sheet. This attracts the toner image powder from the photoconductor surface 12 to the sheet.

After transfer, the paper sheet 24 continues to move onto conveyor 30 advancing the paper sheet to fusing station 32. Fusing station 32 generally includes a heated fuser roller and a backup roller for permanently affixing the transferred powder image to sheet 24. After fusing, paper 24 is advanced to a catch tray 34 for removal by the operator.

Figure 2:
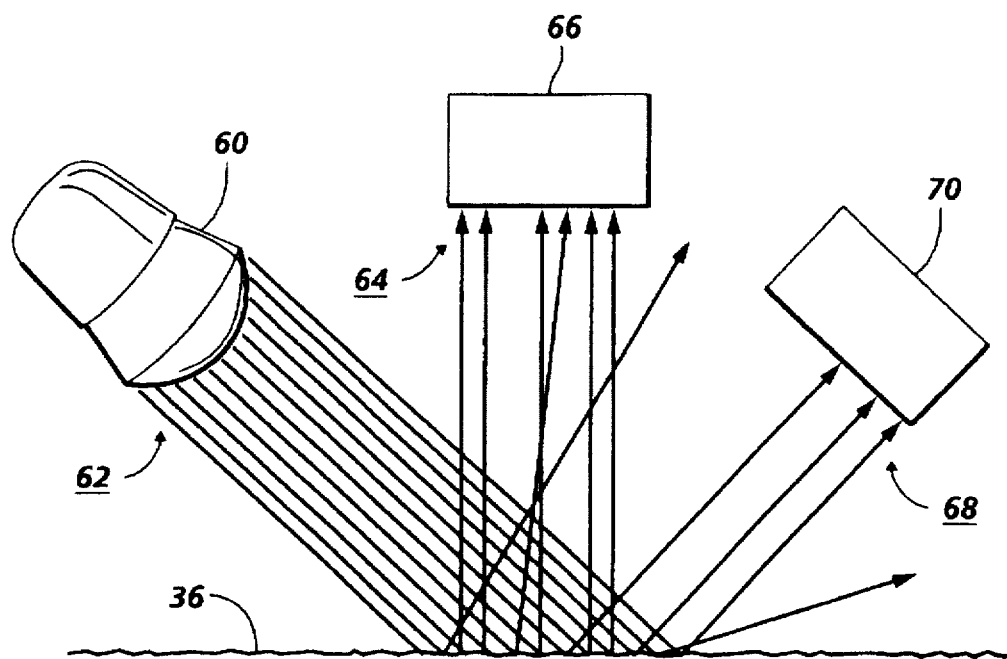
FIG. 2 is a schematic of a light source, sensors and light scattering from a rough surface substrate.

FIG. 2 shows a substrate roughness detection system. A rougher surface paper 36 is shown to illustrate the amount of specularly reflected light 68 versus scattered light 64.

The interactions of light beam 62 from a light source 60 such as a light emitting diode (LED), with substrate 36 can be explained as falling within three broad categories. The first of these categories is that portion of light beam 62 that leaves or escapes the system by the mechanisms of absorption or reflection.

The second category of light, diffuse or scattered light 64, is shown in FIG. 2. Light beam 62 also results in reflection of diffuse light component 64, which is near to isotropically reflected over all possible angles. Light detector, sensor 66, is positioned to receive a portion of diffuse light 64 for detection, measurement and subsequent processing.

The third category of light, specular light 68, is also shown in FIG. 2. Specular light component 68 is the portion of light beam 62 reflected by substrate that is captured by sensor 70. Specular light is reflected according to the well known mechanisms of Snell's law, which states in part that light impinging upon a surface is reflected at an angle equal to the angle of incidence according to the reflectivity of that surface. For a complex, partially transmissive substrate, specularly reflected light may result from multiple internal reflections within the body of the substrate as well as from simple front surface reflection. Thus, an appropriately placed sensor will detect the specular light component. A suitable sensor for measuring both the specular and diffuse components of reflected light is a phototransistor.

Figure 3:
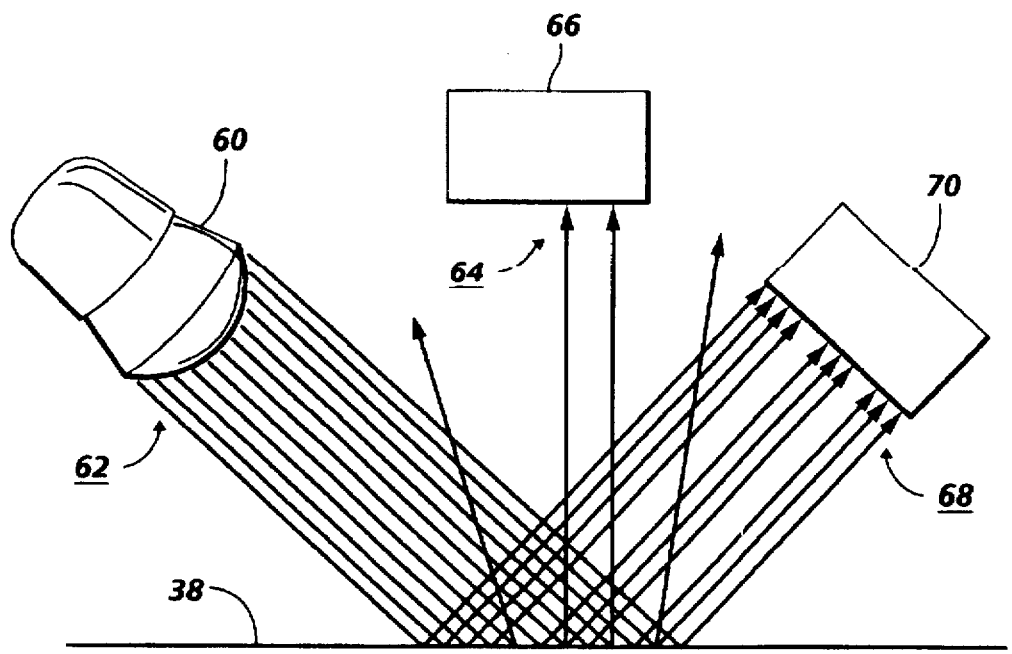
FIG. 3 is a schematic of a light source, sensors and light scattering from a smooth surface substrate.

FIG. 3 shows an optical sensor for determining substrate roughness wherein a smoother surface paper 38 is shown to illustrate the increased amount of specularly reflected light 68 versus scattered light 64, as measured by sensors 70 and 66, respectively.

Figure 4:
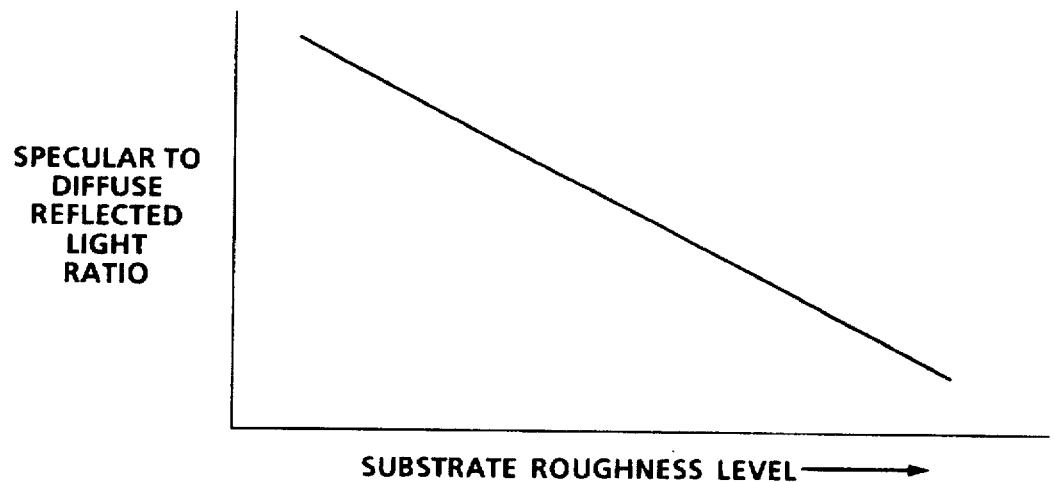
FIG. 4 is a schematic graph showing specular reflection to scattered light ratio versus substrate roughness.

As shown in the graph of FIG. 4, there is a relationship between the ratio of specularly reflected light to diffuse reflected light and the level of substrate roughness. In particular, at a high substrate roughness level, the ratio of specular to diffuse reflected light is small since most of the incident light impinging onto the substrate is attenuated. Namely, the incident light is scattered, thus becoming diffuse light. At a low substrate roughness level, the ratio of specular to diffuse reflected light is large, since a greater amount of incident light impinging onto the substrate is specularly reflected.

Figure 5:
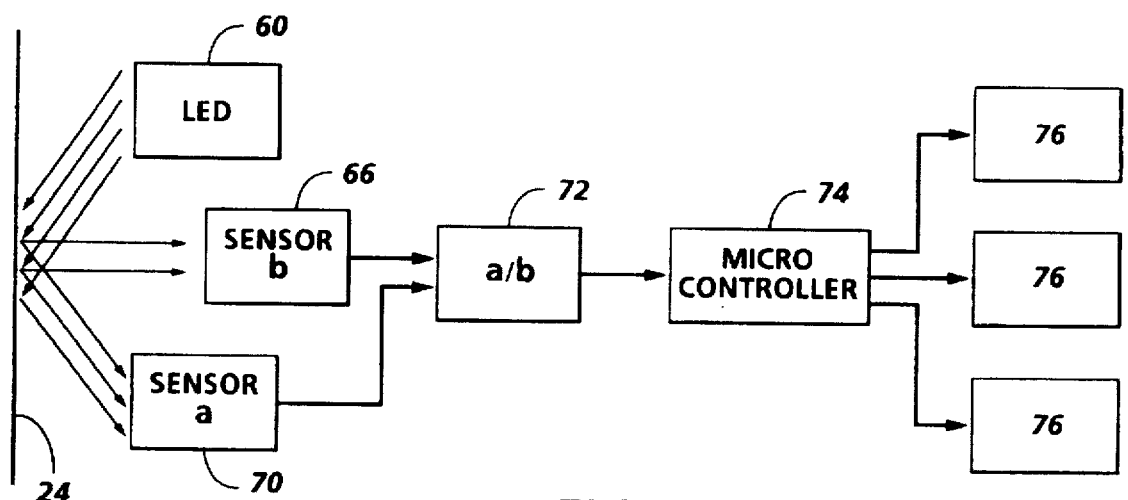
FIG. 5 is an electrical block diagram.

FIG. 5 is an electrical block diagram. Each sensor 66 and 70 produces an output signal indicative of the amount of diffuse and specularly reflected light detected by that sensor. The analog output signal provided by each photosensor 66, 70 is provided to ratio determinator 72 for determining the level of roughness of the substrate. Ideally, the ratio determinator 72 and operation controller 74 can be implemented in a general purpose microprocessor including a CPU, a ROM and a RAM, which are typically used for controlling machine operations in electrophotographic reproduction machines, facsimile machines, printers and the like. Readings from the output signal of the phototransistor 66 and 70 can be stored in the RAM and a ratio value can be derived in the CPU. A higher ratio value of the specularly reflected light to diffuse reflected light indicates a smoother surface substrate, and a lower ratio value indicates a rougher surface substrate.

The output of the ratio determinator 72 can be utilized by an operation controller 74 for controlling processing operations 76 on the substrate 24 on the basis of the detected roughness and appropriate model information concerning processing operations to be affected stored in the ROM. For example, the bias level provided to the corona generating device of the charging station and/or the transfer station 22 can be controlled on the basis of roughness by means of a suitable control algorithm implemented by a microprocessor in the operation controller 74. The design of a suitable controller arrangement and the appropriate programming thereof are influenced by the operation being controlled and can be determined by one of ordinary skill in this art based upon the provided verbal functional description. Therefore, no further detailed description of hardware or software is necessary in order for one of ordinary skill in the art to practice the present, invention without undue experimentation.

The output of the operation controller 74 is provided to the controlled element 76 to vary the operating parameter being controlled. In this regard, the reference to the transfer station 22 is illustrative only, and it should be realized that other operations in a typical electrophotographic reproduction machine, as well as in other types of machines for marking substrates, can be controlled. For example, development voltage and toner concentration associated with the DMA level, and fuser set temperature, are some of the machine parameters known to one skilled in the art that can be regulated with respect to the level of substrate roughness. It will be appreciated that a greater number of system parameters can be controlled and adjusted to their optimum settings based on the roughness level of a particular substrate, from the single sensing device of the present invention.

It will be obvious to one skilled in the art that other machine types for marking onto a substrate that find useful application to the present invention will have corresponding processing operations that can be advantageously adjusted based on the diffuse reflected light sensor 66 and specular reflected light sensor 70 inputs to the ratio determinator 72, and the corresponding output ratio value signal therefrom. It will also be obvious to one skilled in the art, that the output of operation controller 74 can be indirectly provided to the controlled processing operations 76 through an intermediate operator control step.

It is, therefore, evident that there has been provided in accordance with the present invention, a substrate roughness detection apparatus that fully satisfies the aims and advantages hereinbefore set forth. While this invention has been described in conjunction with a specific embodiment thereof, it is evident that many alternatives, modifications and variations will be apparent to those skilled in the art. For example, it can be appreciated that the present invention may find useful application in a paper or other substrate handling machine having processing operations which do not include marking onto the substrate. Accordingly, it is intended to embrace all such alternatives, modifications and variations as fall within the spirit and broad scope of the appended claims.

We claim:

1. An electrophotographic marking machine, comprising:

a photoreceptor;

a corona generating device for charging said photoreceptor;

a first light source for inducing a latent image on said charged photoreceptor;

a developer for developing said latent image by depositing a marking material at a toner concentration on said photoreceptor, wherein said developer receives a control signal that controls the toner concentration;

a fuser for fusing said deposited marking material onto a substrate;

a sheet feeder having a substrate holder, said sheet feeder for moving the substrate from said substrate holder through said fuser;

a second light source for illuminating the substrate;

a first light sensing device for sensing specularly reflected light from the substrate and for generating a first signal in response thereto;

a second light sensing device for sensing diffusely reflected light from the substrate and for generating a second signal in response thereto;

control circuitry operatively connected to said first and second light sensing devices for generating a ratio value of said first and second signals; and an operation controller operatively connected to said control circuitry, said operation controller for receiving said ratio value from said control circuitry and for producing said control signal from said ratio value.

2. The apparatus according to claim 1, wherein said second light source illuminates the substrate when the substrate is in said substrate holder.

\* \* \* \* \*